US00PP09314P

United States Patent [19]

VandenBerg

[11] Patent Number: Plant 9,314

[45] Date of Patent: Oct. 3, 1995

[54] CHRYSANTHEMUM PLANT NAMED 'SHASTA'

[75] Inventor: Cornelis P. VandenBerg, Salinas, Calif.

[73] Assignee: Yoder Brothers, Inc., Barberton, Ohio

[21] Appl. No.: 280,526

[22] Filed: Jul. 26, 1994

[51] Int. Cl.[6] ..... A01H 5/00

[52] U.S. Cl. ..... Plt./82.1

[58] Field of Search ..... Plt./82.1

[56] References Cited

U.S. PATENT DOCUMENTS

| | | | |
|---|---|---|---|
| P.P. 5,984 | 5/1987 | Duffett | Plt./82.1 |
| P.P. 6,058 | 12/1987 | Duffett | Plt./82.1 |
| P.P. 6,590 | 2/1989 | Sueptitz | Plt./82.1 |
| P.P. 7,763 | 1/1992 | VandenBerg | Plt./82.1 |

OTHER PUBLICATIONS

Yoder Products. 1973/74 Edition. p. 39.

Ball Mums. 1970, pp. 37–38.

*Primary Examiner*—Howard J. Locker

*Attorney, Agent, or Firm*—Foley & Lardner

[57] ABSTRACT

A Chrysanthemum plant named Shasta particularly characterized by its flat capitulum form; daisy capitulum type; clear white ray floret color; diameter across face of capitulum of 64 to 70 mm when fully opened, when grown as a pinched spray pot mum; photoperiodic flowering response to short days of 49 to 55 days; plant height, with 14 to 17 long days after sticking unrooted cuttings, and with one application of 2500 ppm B-9 SP, ranges from 18 to 25 cm when grown as a pinched pot mum with four cuttings in a 15 cm pot; branching pattern is spreading and prolific, each plant having 4 to 6 laterals after pinch; and recommended as spray pot mum.

3 Drawing Sheets

The present invention comprises a new and distinct cultivar of Chrysanthemum, botanically known as *Dendranthema grandiflora*, and referred to by the cultivar name Shasta.

Shasta, identified as 6574 (91-012002), was originated from a cross made by Cornelis P. VandenBerg in a controlled breeding program in Salinas, Calif., in 1989.

The female parent of Shasta was the cultivar identified as Denver, disclosed in U.S. Plant Pat. No. 7,763 and described as a pot spray mum with flat capitulum form; daisy capitulum type; clear white ray floret color; diameter across face of capitulum of 57 to 70 mm when grown as a spray pot mum; flowering response to short days in Salinas, Calif. of 48 to 53 days; plant height of 20 to 28 cm when grown with 15 to 18 long days after sticking unrooted cuttings prior to start of short days and 1 to 2 applications of 2500 ppm B-9 SP; and a branching pattern of 4 to 5 laterals developing after pinch.

The male parent of Shasta was an unnamed seedling identified as 1251 (83-742007), and described as a pot spray mum with flat capitulum form; daisy capitulum type; clear white ray floret color; diameter across face of capitulum of 64 to 70 mm when grown as a spray pot mum; flowering response to short days in Salinas, Calif. of 49 to 56 days; plant height of 25 to 33 cm when grown with 14 to 17 long days after sticking unrooted cuttings prior to start of short days, and 1 to 2 applications of 2500 ppm B-9 SP; and a branching pattern of 4 to 5 laterals developing after pinch.

Shasta was discovered and selected as one flowering plant within the progeny of the stated cross by Cornelis P. VandenBerg in July 1991, in a controlled environment in Salinas, Calif.

The first act of asexual reproduction of Shasta was accomplished when vegetative cuttings were taken from the initial selection in September 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Shasta are firmly fixed and are retained through successive generations of asexual reproduction.

Shasta has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Shasta, which, in combination, distinguish this Chrysanthemum as a new and distinct cultivar;

1. Flat capitulum form.
2. Daisy capitulum type.
3. Clear white ray floret color.
4. Diameter across face of capitulum of 64 to 70 mm when fully opened, when grown as a pinched spray pot mum.
5. Photoperiodic flowering response to short days of 49 to 55 days.
6. Plant height, with 14 to 17 long days after sticking unrooted cuttings, and with one application of 2500 ppm B-9 SP, ranges from 18 to 25 cm when grown as a pinched pot mum with four cuttings in a 15 cm pot.
7. Branching pattern is spreading and prolific, each plant having 4 to 6 laterals after pinch.
8. Recommended as spray pot mum.
9. Shasta has a contrasting green disc that very slowly develops to green-yellow.

The accompanying photographic drawings show typical inflorescence and leaf characteristics of Shasta, with the colors being as nearly true as possible with illustrations of this type.

Sheet 1 is a color photograph of Shasta grown as a pinched spray pot mum with four cuttings in a 15 cm pot.

Sheet 2 is a black and white photograph of three views of the inflorescence of Shasta.

Sheet 3 is a black and white photograph showing the upper and under sides of the leaves of Shasta at 3 stages of development (mature, intermediate and immature).

In sheets 2 and 3 a measuring tape in centimeters has been added.

Of the commercial cultivars known to the inventor, the most similar in comparison to Shasta is the cultivar identified as Solo, disclosed in U.S. Plant Pat. No. 6,058. Reference is made to attached Chart A, which compares certain characteristics of Shasta to the same characteristics of Solo.

Similar traits are capitulum form and type, and recommendation as spray pot mum. The ray floret color of both Shasta and Solo is white. However, the ray floret color of Shasta is a very clear white, while the ray floret color of Solo is an off-white, described as RHS 155B. Shasta also has a larger diameter of capitulum, is slightly slower in flowering response to short day by 1 to 2 days, and has a shorter plant height when compared with Solo. In comparison to Denver, Shasta has a flowering response that is 1 to 2 days slower than that of Denver. Although Denver is 2 to 3 cm taller than Shasta with 14 to 18 long days, the plant habit of Shasta is more spreading than that of Denver because Shasta develops more laterals after pinching than Denver.

In the following description color references are made to The Royal Horticultural Society Colour Chart. The clear white ray floret color of Shasta is not represented in the R.H.S. Colour Chart. The color values were determined on plant material grown as a pinched spray pot mum in Salinas, Calif. on Apr. 29, 1994.

Classification:

*Botanical.*—*Dendranthema grandiflora* cv Shasta.

*Commercial.*—Daisy spray pot mum.

INFLORESCENCE

A. Capitulum:

*Form.*—Flat.

*Type.*—Daisy.

*Diameter across face.*—64 to 70 mm when fully opened.

B. Corolla of ray florets:

*Color (general tonality from a distance of three meters).*—Whiter than RHS 155D.

*Color (upper surface).*—Whiter than RHS 155D.

*Color (under surface).*—Whiter than RHS 155D.

*Shape.*—Longitudinally straight and in cross-section flat to slightly convex on outer ray florets.

C. Corolla of disc florets:

*Color (mature).*—14B.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—18 to 25 cm when grown as a pinched pot mum with four cuttings in a 15 cm pot, and with 14 to 17 long days after direct sticking unrooted cuttings prior to start of short days and 1 application of 2500 ppm B-9 SP.

*Branching pattern.*—Spreading and prolific, with 4 to 6 laterals developing after pinch.

B. Foliage:

*Color (upper surface).*—147A.

*Color (under surface).*—147B.

*Shape.*—Deeply lobed and strongly serrated.

CHART A
COMPARISON OF SHASTA AND SOLO

| CULTIVAR | SHASTA | SOLO |
|---|---|---|
| Ray floret color | Clear white | White |
| Capitulum form and type | Flat daisy | Flat daisy |
| Diameter across face of capitulum | 64 to 70 mm | 54 to 67 mm |
| Flowering response | 49 to 55 days | 48 to 53 days |
| Plant height with 14 to 18 long days | 18 to 25 cm | 20 to 28 cm |
| Branching pattern | 4 to 6 laterals | 4 to 6 laterals |
| Recommended as | Pot spray mum | Pot spray mum |

COMPARISONS MADE OF PLANTS GROWN AS PINCHED SPRAY POT MUMS IN SALINAS, CALIFORNIA

I claim:

1. A new and distinct Chrysanthemum plant named Shasta, as described and illustrated.

* * * * *

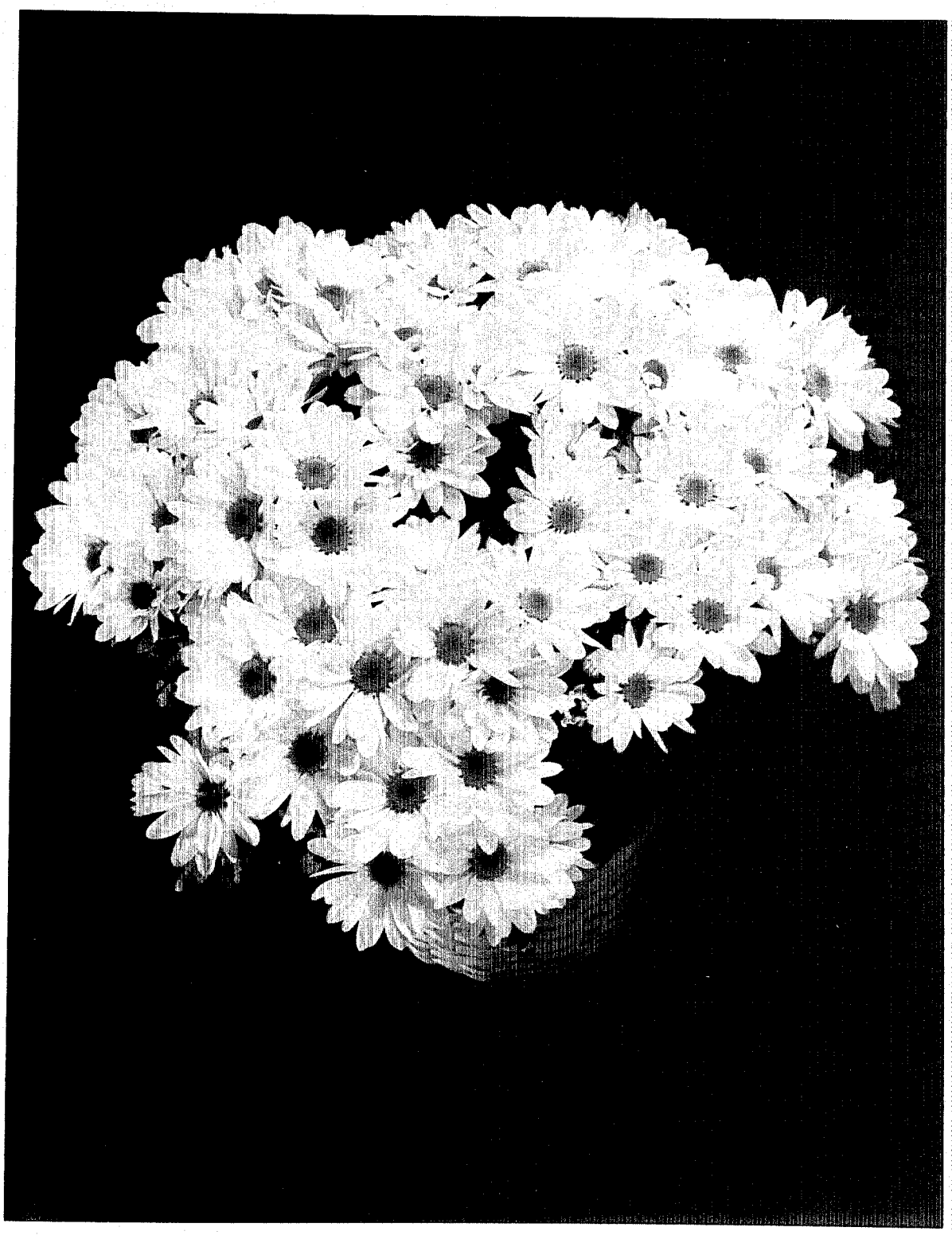

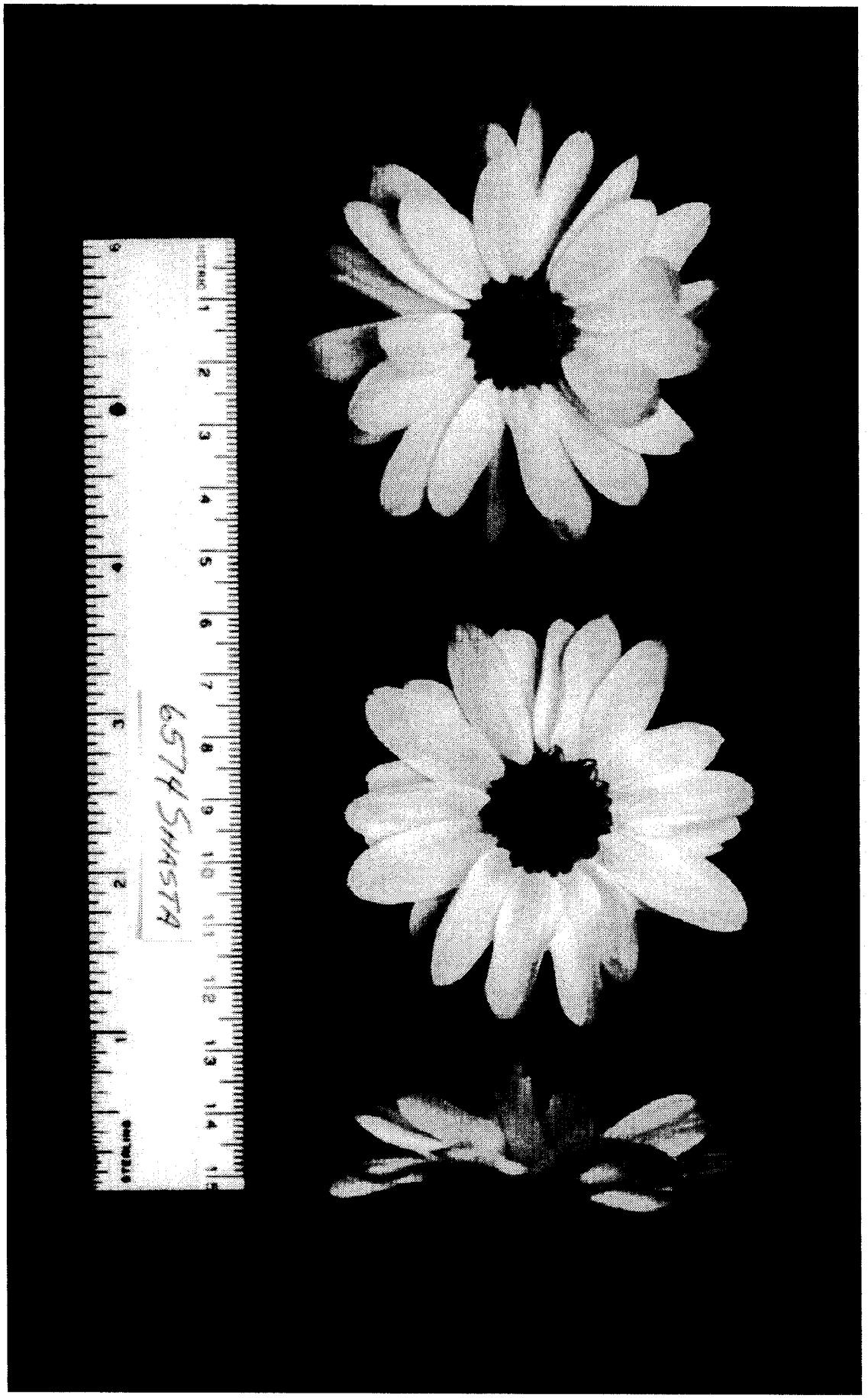
6574 Shasta

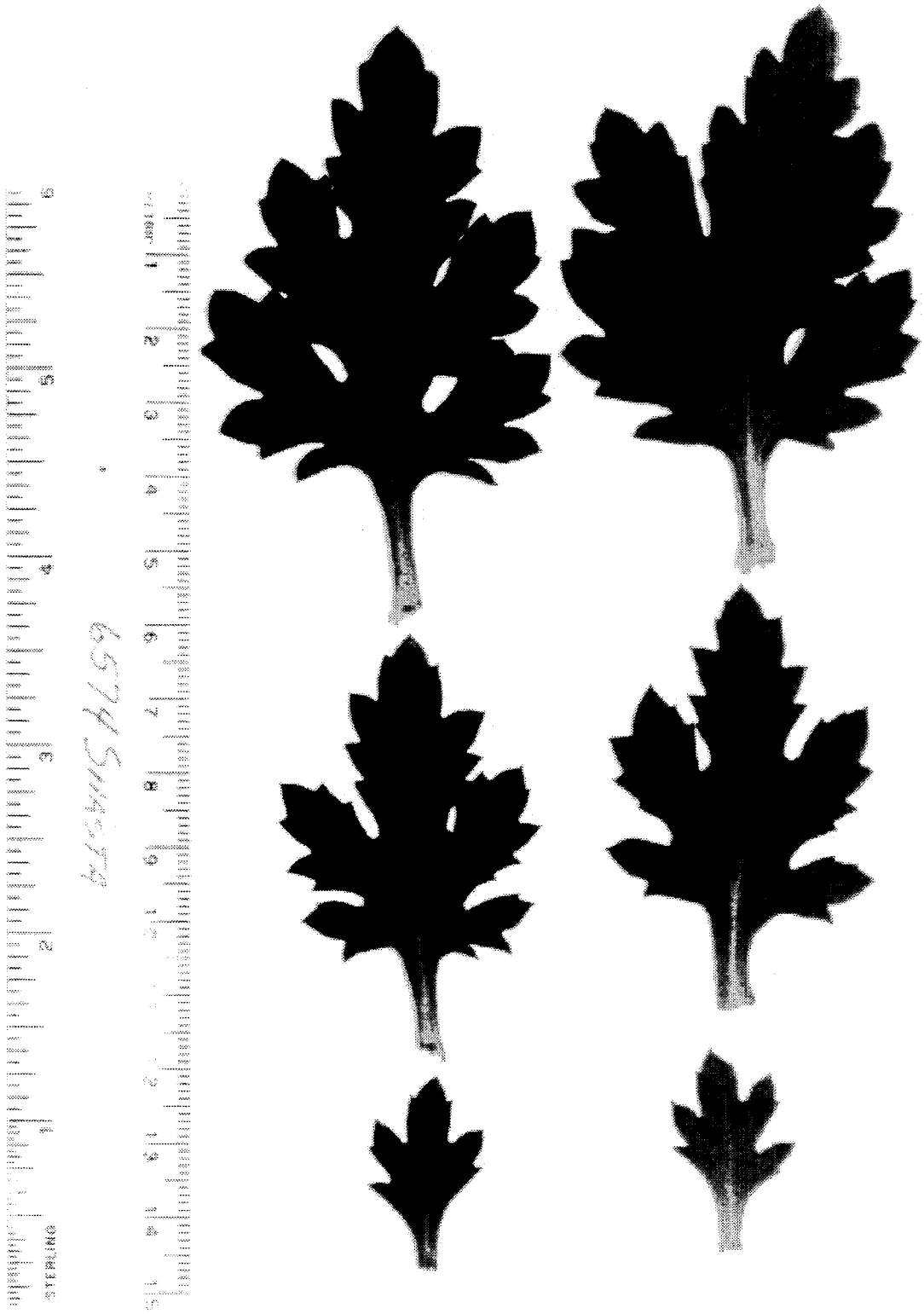
STERLING
6579 Smith